(12) United States Patent
Hollenberg et al.

(10) Patent No.: US 7,387,795 B2
(45) Date of Patent: Jun. 17, 2008

(54) COSMETIC COMPOSITIONS ORGANOPHOSPHONIC ACID COATED PARTICULATES AND METHODS FOR PRODUCING THE SAME

(76) Inventors: Jane Hollenberg, 40 Cherry St., Red Hook, NY (US) 12571; Anthony Parker, 10 Columbine Cir., Newton, PA (US) 18940

( * ) Notice: Subject to any disclaimer, the term of this patent is extended or adjusted under 35 U.S.C. 154(b) by 665 days.

(21) Appl. No.: 10/852,051

(22) Filed: May 24, 2004

(65) Prior Publication Data

US 2004/0265348 A1   Dec. 30, 2004

Related U.S. Application Data

(60) Provisional application No. 60/475,960, filed on Jun. 5, 2003.

(51) Int. Cl.
*A61K 8/02*     (2006.01)
*A61K 9/14*     (2006.01)
*A61Q 17/04*    (2006.01)

(52) U.S. Cl. .................. 424/490; 424/489; 424/401; 424/59; 514/937; 514/938

(58) Field of Classification Search ............ 424/401, 424/489, 490, 601, 605, 59, 61, 64, 70.7; 514/844, 845, 937, 938, 951, 937.938
See application file for complete search history.

(56) References Cited

U.S. PATENT DOCUMENTS

| 4,578,266 | A | | 3/1986 | Tietjen |
| 4,877,604 | A | | 10/1989 | Schlossman |
| 5,059,258 | A | | 10/1991 | Wefers et al. |
| 5,108,736 | A | | 4/1992 | Schlossman |
| 5,143,722 | A | | 9/1992 | Hollenberg et al. |
| 5,348,760 | A | | 9/1994 | Parker |
| 5,543,173 | A | | 8/1996 | Horn et al. |
| 5,599,530 | A | | 2/1997 | Patil et al. |
| 5,609,852 | A | * | 3/1997 | Galley et al. .............. 424/59 |
| 5,837,049 | A | * | 11/1998 | Watson et al. .............. 106/427 |
| 6,214,106 | B1 | | 4/2001 | Weber et al. |
| 6,315,990 | B1 | | 11/2001 | Farer et al. |

* cited by examiner

*Primary Examiner*—Johann R. Richter
*Assistant Examiner*—Konata M George
(74) *Attorney, Agent, or Firm*—Marshall & Melhorn, LLC

(57) ABSTRACT

The invention provides cosmetic compositions containing powders that are surface treated with organophosphonic acid compounds, where the surface treated particulates are simultaneously hydrophobic and lipophilic. The invention also provides (a) methods for preparing cosmetic compositions containing said powders, and (b) methods for preparing cosmetic compositions containing said powders where the powders have been treated via a volatile organic solvent-free manufacturing process.

13 Claims, No Drawings

COSMETIC COMPOSITIONS ORGANOPHOSPHONIC ACID COATED PARTICULATES AND METHODS FOR PRODUCING THE SAME

RELATED APPLICATION

This application is claiming the benefit, under 35 U.S.C. § 119(e), of the provisional application filed Jun. 5, 2003 under 35 U.S.C. § 111(b), which was granted Ser. No. 60/475,960. This provisional application is hereby incorporated by reference in its entirety.

BACKGROUND OF THE INVENTION

Cosmetic compositions are provided which contain organophosphonic acid surface treated particulates. The powders are characterized as being pigments or fillers for said compositions. When surface treated, the powders are essentially hydrophobic in the sense that they repel water (i.e., they do not disperse in water), whereas in the absence of surface treatment, the same powders are observed to disperse in water. Simultaneously, the surface treated powders are essentially lipophilic, and hence exhibit improved dispersion characteristics in oily media commonly used in cosmetics, including silicones, hydrocarbons, natural esters, and synthetic esters.

The advantages of cosmetics compositions that contain pigments with such characteristics have been described in the prior art by several inventors. For example, Schlossman in U.S. Pat. No. 4,877,604 used titanate treated powders to achieve cosmetic compositions with (a) improved dispersion characteristics, (b) with the capacity for higher inorganic loadings, (c) with less settling and improved shelf stability, (d) with increased "smoothness" upon application, (e) with improved skin adhesion, and (f) with improved moisture resistance in the final skin application. Hollenberg, et al. in U.S. Pat. No. 5,143,722 disclosed similar improvements that were achieved via reactive polysiloxane or organosilane surface-treated pigments. In addition, fluorosilane surface treatments were used for the achievement of simultaneous hydrophobicity and lipophobicity by Farer, et al. in U.S. Pat. No. 6,315,990. Similarly, organometallic zirconium compounds have been used to achieve improved cosmetic compositions as taught by Patil, et al. in U.S. Pat. No. 5,599,530.

Although the prior-art cosmetics compositions share many advantages, they also share common shortcomings. For example, undesirable byproducts such as volatile organic compounds (VOC's), hydrochloric acid, or hydrogen are often evolved during the process of manufacturing the surface treated powders that are used in such compositions. When solvent-based carriers are used, environmental concerns can sometimes arise since the solvents must be volatilized during the later stages of manufacturing (i.e., during the drying process). In certain cases, and depending on the chemical nature and quantity of the solvent carrier, some of these volatile organic compounds can remain adsorbed on the particle surfaces together with unwanted by-products of oxidation. Also, even in the absence of organic solvent carriers, the nature of the hydrolysis and condensation reactions of many neat prior-art compounds leads to the inevitable evolution of volatile organic compounds, or other potentially deleterious reaction by-products. For example, when a surface treatment is performed by mixing and reacting polyhydrogensiloxanes with dry powders (as described by Hollenberg et al. in U.S. Pat. No. 5,143,722), or by dry blending n-octyltrialkoxysilane with inorganic powders as taught by Horn et al. in U.S. Pat. No. 5,543,173; incomplete hydrolysis can lead to the slow release of either hydrogen or VOC's over time (i.e., during the storage of the treated powders, or during the storage of finished products that contain the treated powders). When an alternative surface treatment is used such as an organohalosilane as taught by Weber, et al. in U.S. Pat. No. 6,214,106, the by-products include halogen salts such as hydrogen chloride, which can also be deleterious in many end-use applications.

BRIEF SUMMARY OF THE INVENTION

In contrast to the prior art, the current invention provides for cosmetic compositions comprising surface treated particulates, wherein either all or a portion of said particulates are partially or completely surface treated with an organophosphonic acid compound. Preferably, the surface treatment compounds and preparation methods are chosen so as to reduce or eliminate the possibility of producing and retaining residual hazardous byproducts. Furthermore, the current invention makes use of surface treated powders that retain their hydrophobic characteristics and are stable in the presence of water for long periods of time, and as such there are no storage restrictions for cosmetics compositions that are prepared with them.

Specifically, the cosmetics compositions of the present invention make use of alkylphosphonic acid treated powders, whereby the powders by definition are devoid of the deleterious reaction by-products that are otherwise characteristic of the prior art surface treatments. The alkylphosphonic acid treated powders also exhibit unexpected combinations of hydrophobic and lipophilic characteristics. The term "lipophilic" in this context means that the powder particle surfaces are easily wetted and dispersed within the liquid oils that are commonly used in cosmetic compositions. The term "hydrophobic" in this context means that the powders have the ability to completely repel water (as evidenced by the formation of a segregated partition between the pigment and the water-phase; such that the water-phase remains clear, and does not become cloudy when the two are mixed). It is to be appreciated that although many powders of the prior-art are lipophilic, not all of them are simultaneously hydrophobic; i.e., not all lipophilic powders have the ability to repel water. The simultaneous achievement of these characteristics is an important aspect of this invention, especially since these simultaneous characteristics are highly desirable for producing many types of cosmetics compositions (as noted by Hollenberg et al. in U.S. Pat. No. 5,143,722), including those provided by the present invention.

The cosmetic compositions of the present invention can be prepared with pigments that have been surface treated with an alkylphosphonic acid, where the alkylphosphonic acid may be applied by means of either an organic solvent or a water-based carrier. Surprisingly, either type of carrier can be equivalently employed for the purposes of achieving the unique hydrophobic and lipophilic characteristics that are desirable for producing the cosmetic compositions of the present invention. Given the relatively poor solubility of alkylphosphonic acids in water, it is surprising to note that hydrophobic characteristics are achieved from powders that are treated with solely water based mixtures. In fact, it is plausible to anticipate that heterogeneous mixtures such as these might lead to heterogeneous surface coverage, where the resultant properties of the heterogeneously treated powders would be inferior to those treated with otherwise homogeneous surface treatment solutions. However, this is surprisingly not the case. For example, in spite of the partial solubility of n-octylphosphonic acid in water (an opaque, viscous, emulsion-like mixture forms when n-octylphosphonic acid is added to water at concentrations of greater than about 10% by weight), the resultant surface coverage is unexpectedly efficient. In fact, the resultant powders are completely hydrophobic, and dispersible in oil. Moreover, similar results are achieved when a completely soluble solution of n-octylphosphonic acid in isopropyl alcohol is used in place of a water-based mixture. Thus, partially soluble mixtures of alkylphosphonic acid in water yield surface treated pigments that are unexpectedly on par with those obtained through the use of completely miscible treatment solutions.

It is equally surprising to note that when the treatment is applied through a water medium, the resultant treated powders tend to repel and not disperse in water, and the treatment remains intact even when the treated powders are exposed to water for long periods of time. Moreover, in cases where the neat alkylphosphonic acid is itself soluble in a hydrophobic solvent medium, the successfully treated powders remain unexpectedly dispersible in the same medium even after several attempts have been made to remove the surface treatment (through repeated washing with virgin aliquots of the same hydrophobic solvent). Thus, once the treated powders are formed, the treatment is unexpectedly stable and resistant to removal by both water and oil. It is to be appreciated that pigments with these attributes are paramount to the achievement of stable water-in-oil and oil-in-water cosmetics compositions (as taught by Hollenberg et al. in U.S. Pat. No. 5,143,722). Consequently, alkylphosphonic acid treated particulates with these attributes are important components for use in the cosmetic compositions as defined by the present invention.

A neat alkylphosphonic acid compound can also be used to prepare the powders for use in this invention; and in such cases, it is preferable to heat the neat compound above its melt point and to mix it with the powder while the compound is in its molten state. Similarly, when water-based mixtures are used, the mixtures can be heated to improve solubility and to reduce viscosity. In such cases, heated mixtures can be mixed directly with the powder either at ambient or at elevated temperatures.

The combined hydrophobic/lipophilic characteristics that are imparted by alkylphosphonic acid treated pigments are surprisingly unique and cannot be anticipated from the behavior of pigments that have been surface treated with analogous compounds. Although organophosphonic acids have been shown to chemically adsorb onto certain inorganic materials (i.e., onto aluminum as shown by Wefers, et al., U.S. Pat. No. 5,059,258; and onto titanium dioxide as shown by Watson, et al. in U.S. Pat. No. 5,837,049), the comparative examples provided herein demonstrate that chemical adsorption alone and/or surface polymerization are not predictors of, nor are they prerequisites for the simultaneous achievement of the hydrophobicity and lipophilicity that are paramount to this invention. For example, monomeric alkylcarboxylic acids are known from the prior-art to adsorb onto pigment surfaces, and to impart lipophilicity, but the hydrophobic characteristics of such treated pigments are surprisingly inferior to those treated with analogous monomeric alkylphosphonic acids. By contrast, the hydrophobic and lipophilic characteristics imparted by alkylphosphonic acids are surprisingly similar to those imparted by alkyltrialkoxysilanes; but unlike the alkylphosphonic acids, the alkyltrialkoxysilanes are known to hydrolyze and polymerize on the surfaces of inorganic pigments. Thus, there is no known mechanism by which one can predict the simultaneous achievement of hydrophobicity and lipophilicity as has been surprisingly achieved through the use of alkylphosphonic acid modified pigments.

Thus, in one aspect the invention provides cosmetics compositions that contain organophosphonic acid surface treated particulates, where the particulates possess lipophilic, or simultaneously hydrophobic and lipophilic characteristics. Methods of producing such compositions are also provided.

In another aspect of this invention, cosmetics compositions are provided that comprise organophosphonic acid surface treated particulates, whereby the organophosphonic acid treated particulates are produced via a volatile organic solvent-free process, and where the surface treated particulates possess simultaneous hydrophobic and lipophilic characteristics.

In a further aspect of the invention, cosmetic compositions are provided having particulates, where at least some of which, if not all of which, are coated with an organophosphonic acid.

DETAILED DESCRIPTION OF THE INVENTION

The cosmetic compositions of this invention are prepared with pigments that have been surface treated with organophosphonic acids. The organophosphonic acid surface treatments may be monomeric, oligomeric, or polymeric as described by the general formula:

$$R_x[PO(OH)_2]_y$$

where R is an organic group containing 1 to 50 carbon atoms, x is the number of organic groups (about 1-30), and y is the number of phosphonic acid groups (about 1-20). Examples of suitable monomeric organophosphonic acid compounds (where x & y=1) include methylphosphonic acid, ethylphosphonic acid, butylphosphonic acid, octylphosphonic acid, dodecylphosphonic acid, and octadecylphosphonic acid.

The R group can be generally comprised of long or short chain aliphatic hydrocarbons, aromatic hydrocarbons, styrenic, vinyl, carboxylic acids, aldehydes, ketones, amines, amides, imides, lactams, carbohydrates, esters, lactones, ethers, alkenes, alcohols, nitriles, ureas, organosilicones, perfluoro organic groups, silanes, and others as well as combinations of these groups. In addition, the R group can be a polymeric structure that contains y phosphonic acid groups. Examples of representative structures include products of monomeric phosphonic acid homopolymerization such as polyvinylphosphonic acid, poly(vinylbenzyl)phosphonic acid; products of copolymerization of such monomers with other types of monomers; and polymeric molecules that have been functionalized with phosphonic acid moieties through post polymerization processes.

The surface treatments can also include organophosphinic acids of the general formula $$R_x[PO(OH)]_y$$

where R is an organic group like that described above.

In addition, pigments can be optionally pre-treated with appropriate acidic or basic solutions prior to treatment with an organophosphonic acid compound; wherein such pre-treatments may improve the performance of the final treated pigment for the purposes of this invention. Furthermore, the pigments can be optionally co-treated with other compounds for the purpose of imparting additional functionality or utility to the resultant particle surfaces. Such co-treatments can include but are not limited to organosilanes, carboxylic acids and their salts, titanates, zirconoates, organoaluminum compounds, aluminum salts, aluminum trichloride, aluminum trihydrate, azole and imidazole compounds, etc. These optional co-treatments can be applied either before the application, after the application, or in combination with the application of the preferred organophosphonic acid surface treatments of the present invention. Also, pigments that are treated with functionalized organophosphonic acids can be optionally reacted with other organic compounds to produce grafted surface treatments. For example, a vinylphosphonic acid treated particulate could be subsequently exposed to a reaction medium whereby in the presence of the appropriate catalyst (such as an organic peroxide, or in certain cases, a redox catalyst which could include the pigment itself as a co-catalyst component), the vinyl groups can be made to undergo polymerization or copolymerization with various monomers to form polymeric grafts with block copolymer, random copolymer, or homopolymer structural characteristics.

Suitable pigments include all inorganic and organic pigments or fillers that are usable in cosmetic compositions. Particular examples include titanium dioxide (rutile or anatase forms), ferric oxide and its hydrates, ferrous oxide, chromium oxide, chromium hydroxide, zinc oxide, aluminum oxide, aluminum trihydrate, calcium carbonate, magnesium carbonate, calcium silicate, silica, manganese violet, talc, mica, kaolin, ultramarines, and their equivalents. Other examples include but are not limited to lakes of organic colorants such as D & C. Red No. 7 calcium lake, D&C Red #6 barium lake, FD & C Yellow No. 5 aluminum lake, FD & C Blue No.1 aluminum lake, D & C Red No. 6 barium lake, and D&C Red No. 30, etc.

The pigment materials to be treated in accordance with the present invention may be provided in a range of particle sizes, shapes, surface areas, and particle size distributions. In treating such powders, a sufficient level of organophosphonic acid surface treatment should be used so as to achieve nearly a monolayer of surface coverage. Although the exact level depends on the surface area and chemical nature of the powder, this condition is preferably met with surface concentrations ranging from about 1-30 $\mu$moles/m$^2$, and more preferably with surface concentrations ranging from about 2-15 $\mu$moles/m$^2$, and most preferably with surface concentrations ranging from 5-11 $\mu$moles/m$^2$. However, it is important for the purposes of this invention to not exceed the level required for hydrophobicity (as measured by the tendency of the treated pigment to repel and not disperse in water), otherwise the treated pigment may become surprisingly hydrophilic. On the other hand, it is to be recognized that such pigments may still be particularly useful, especially when lipophilicity is the primary objective. Using the case of titanium dioxide as an example, partial hydrophobicity is achieved with as little as about 2 $\mu$moles/m$^2$ of n-octylphosphonic acid surface treatment; complete hydrophobicity is achieved at surface concentrations ranging from about 5 and 12 $\mu$moles/m$^2$; and increasingly hydrophilic powders are obtained as concentrations are increased beyond about 20 $\mu$moles/m$^2$. Surprisingly however, regardless of whether the treatment is controlled to yield a hydrophobic or hydrophilic powder, the resultant lipophilicity and oil-phase dispersion characteristics are still improved.

The surface treatments of this invention can be dissolved in numerous carrier solvents for the purpose of coating the pigments. A suitable solvent can include any organic solvent that completely or partially dissolves the organophosphonic acid; examples of which include isopropyl alcohol, ethanol, methanol, and mixtures of such alcohols with water. However, one of the advantages of this invention is that water alone can be used as the carrier, even though for example certain organophosphonic acids such as n-octylphosphonic acid are only partially soluble in water. In such cases, the organophosphonic acid can be mixed with water over any range of concentrations to yield completely soluble solutions in the dilute extreme, and to yield opaque and partially soluble slurries in the concentrated extreme. Concentrated slurries can be optionally heated to temperatures ranging from about 50-90° C. to improve solubility and to reduce viscosity. After heating, the mixtures can be cooled to room temperature before they are applied to the pigment, or they can be applied to the pigment while hot. The pigment itself can also be conditioned at ambient or at elevated temperatures prior to being mixed with the treatment slurry.

The desirable concentration of the treatment slurry (or solution) depends upon the treatment process that is to be employed. In one extreme, a wet process can be used where sufficient carrier solvent can be employed so as to completely disperse the pigment. Mixing and drying procedures can be followed as described in the prior art through the sequential use of ball mills, shear mixers, drying ovens, and the like.

However, in keeping with the advantages of this invention, it is most preferable to use dry-blending processes such as those that are known in the art; including, but not limited to those described by Hollenberg, et al. in U.S. Pat. No. 5,143, 722, by Horn et al. in U.S. Pat. No. 5,543,173, and by Parker et al. in U.S. Pat. No. 5,348,760; where sufficient dry-blending treatments are achieved through the use of tumbling blenders, ball mills, high shear mixers, hammer mills, and combinations thereof; and where the use of carrier solvents is minimized.

In one preferred dry-blend process, the carrier is water, and the organophosphonic acid/water slurry is as concentrated as is practical for the purposes of achieving both a homogenous mixture and a homogeneous surface treated product. In such a process, the concentrated slurry is added to the dry powder while the mixture is tumbled, ball milled, shear mixed, or the like for a sufficient time so as to achieve adequate surface coverage. "Adequate surface coverage" for the purposes of this invention can be determined via "hydrophobicity" and "lipophilicity" tests as described herein. Once sufficient blending is achieved, the powder is dried (for example in a gravity or forced air oven) at a temperature between about 50° and 105° C. for a time that is both sufficient to remove excess water; and sufficient to achieve the desired levels of hydrophobicity and lipophilicity; where the desired level of hydrophobicity is determined by the pigment's tendency to repel from water (as evidenced by the formation of a segregated partition between the pigment and the water-phase; such that the water-phase remains clear, and not cloudy when the two are mixed); and the desired level of lipophilicity is determined by the sedimentation density of the pigment in a lipophilic dispersion medium of choice (using the sedimentation methods as described by Parker in *The Journal of Adhesion Science and Technology*, 16, 2002, pp.679-701; and by Parker et al. in *Material Research Society Symposium Proceedings*, 249, 1992, pp.273-278).

In another variant of the dry-blend process, the carrier for the alkylphosphonic acid may be an alcohol such as isopropanol, or an isopropanol/water solution. The preferred processes for preparing powders with such carriers are completely analogous to the preferred processes that are employed when water is used as the carrier. However, if a solvent carrier is employed, it is most desirable to use a treatment solution where the alkylphosphonic acid concentration is as high as possible so as to minimize the level of organic solvent that must otherwise be removed during the drying process.

The concentration for the alkylphosphonic acid treatment solution or mixture must also be practical from the standpoint of achieving adequate blending efficiency and surface coverage in a dry-blend process. For example, at higher concentrations in water (i.e. at higher ratios of alkylphosphonic acid to water), the viscosity of the mixture could make it more difficult to achieve a homogenous dry-blend, and the process may require longer periods of time. On the other hand, the viscosity of an alkylphosphonic acid/water mixture can be reduced by raising the temperature of the slurry, by increasing the temperature of the powder, or by doing both in combination. Although higher concentrations could be employed, the preferred slurry concentration for ambient or elevated temperature blending is 5% to 50% by weight n-octylphosphonic acid in water, or more preferably 5% to 25% by weight, and most preferably about 16-20% by weight n-octylphosphonic acid in water. The preferred slurry concentrate can either be added all at once to the dry powder, or it can be metered into the blending apparatus over time. Turning again to the case of titanium dioxide as an example, adequate hydrophobicity and lipophilicity are achieved when a 16.67% by weight slurry of n-octylphosphonic acid (NOPA) in water is added at a level sufficient so as to achieve between 1% and 2% residual NOPA by weight powder after drying (this equates to approximately 6-12 g of concentrated slurry per 100 g of titanium dioxide). For cases where the alkylphosphonic acid forms a miscible solution with the solvent carrier (as is the case with isopropanol and NOPA), higher surface treatment solutions can be employed during the dry-blend process. For example, when a 70/30 (v/v) blend of isopropyl alcohol and water is used as the carrier, a completely miscible solution containing about 25% by weight NOPA may be successfully used as the treatment solution. It can be appreciated that even higher concentrations could be employed, as long as adequate surface coverage is achieved (as measured by the hydrophobicity and lipophilicity tests that are described herein).

The surface treatments of this invention can be optionally dry-blended with pigments in the absence of a carrier, as long as sufficient surface coverage is achieved in the process. In such cases, the efficiency of surface coverage can be improved by increasing either the temperature of the phosphonic acid compound, the temperature of the powder, or the temperature of both in combination; where the preferred temperature is near or above the crystalline melt point of the organophosphonic acid compound.

In addition, treatments can optionally be performed through spray methods, or through integral blend methods. An integral blend method of preparing the cosmetic compositions of the present invention may include several steps, where for example in a first step 1) the particulates are mixed, blended, or dispersed together with all or a portion of the ingredients of the cosmetic composition, and in a second step 2) an organophosphonic acid compound is integrally blended with all or a portion of the premixed ingredients from step 1, and whereby if portions are premixed in either steps 1 and 2, then an optional third step is employed 3) where the finished premixed portions from steps 1 and 2 are mixed, blended, or dispersed together to achieve the final cosmetic composition.

The cosmetic compositions of the present invention are useful in a variety of products, including foundations, eyeshadows, blushes, mascara, eyeliners, skin treatment products, sunscreens, nail enamels, powder compacts, and so on. Powders are prepared whereby the filler pigments and/or the pigments are pre-treated with alkyl phosphonic acid, rendering them lipophilic and optionally hydrophobic. Dispersed systems are comprised of organophosphonic acid treated pigments that are distributed in the appropriate cosmetically acceptable carrier; where the dispersion medium of such carriers can include various oils, solvents, wax/oil blends, and combinations leading to water-in-oil, or oil-in-water emulsions.

In one preferred embodiment, the treated pigments are lipophilic, and in another particularly preferred embodiment, the treated pigments are simultaneously lipophilic and hydrophobic. Either way, the treated pigments are preferably dispersed in the oil phase of a water-in-oil emulsion at a level of 2% to 50% by weight of the oil phase, and more preferably at about 30% by weight. The oil phase may also contain oil soluble components as are common to personal care products; including for example: preservatives (e.g. up to 0.5 weight percent of the oil phase of paraben such as propyl paraben); up to 1 percent by weight of the oil phase of any conventional cosmetically acceptable fragrance; and one or more of other components well-known to cosmetic chemists, such as those that are intended for cosmetic purposes, or for skin-softening and/or for physiological purposes (e.g. for treating skin conditions, like dry skin or chapped skin).

The oil phase may contain one or more polysiloxanes (either linear or cyclic, volatile or non-volatile, or in any combination). Additionally, the oil phase may contain volatile or non-volatile hydrocarbons of vegetable origin, and/or of mineral or synthetic origin, such as mineral oil, polydecene, polybutene, perhydrosqualene, hydrogenated polybutene, hydrogenated polydecene, isoparaffins, etc.; and hydrocarbon waxes such as petrolatum, ozokerite, microcrystalline-types, polyethylene, and paraffin wax. Other examples of oil-soluble personal-care components that are useful in the compositions of this invention include, but are not limited to ester waxes, oils and fats of animal or vegetable origin, such as spermaceti wax; beeswax, carnauba wax, lanolin wax, avocado oil, coconut oil, castor oil and lanolin oil; fatty alcohols such as cetyl alcohol, isostearyl alcohol, octyldodecyl alcohol, stearyl alcohol and lauryl alcohol; fatty acids such as stearic acid, isostearic acid, and palmitic acid; short and long chain alkyl esters of fatty acids such as the isopropyl, ethylhexyl, octyldodecyl esters of said fatty acids; and sunscreens such as octyldimethyl-PABA, octylmethoxycinnamate, benzophenones, octyl salicylate, homomenthyl salicylate, etc.

The compositions preferably contain surfactants for the purpose of maintaining emulsion stability. For the case of a water-in-oil composition, the surfactant must be capable of maintaining a stable water-in-oil emulsion both during the manufacturing process, and during end-use. A silicone-based surfactant with an HLB value of about 2.5 to about 6 may suffice (examples of which are given in U.S. Pat. No. 5,143, 722); or non-silicone surfactants (with typical HLB values ranging from 2 to 12) may be used either alone or in combination with such silicone-based surfactants. Preferred silicone surfactants are polydiorganosiloxane-polyoxyalkylene copolymers, having International Cosmetic Nomenclature names such as PEG/PPG-18/18 Dimethicone, bis-PEG/PPG-14/14 Dimethicone, Cetyl PEG/PG-10/1 Dimethicone, Lauryl PEG/PPG-18/18, Lauryl PEG/PPG-18/18 Methicone, Dimethicone/Vinyl Dimethicone Crosspolymer, etc.

Examples of non-silicone surfactants can include those known to the art, provided that the overall effective HLB value still permits formation of the desired water-in-oil emulsion. The amount should be about 0.25 to 5.0 weight percent of the composition, and preferably 0.5 to 2.0 weight percent thereof. As is well known to those of ordinary skill in this art, the HLB value is determined by a standardized technique for measuring the solubility of a surfactant. Said surfactant may be anionic, cationic or non-ionic with respect to its hydrophilic portion. Satisfactory surfactants useful in this invention include ethoxylated polyhydroxystearate esters, low mole ethoxylated alkylene ethers, glyceryl monooleate, polyglyceryl esters, and sorbitan esters. Other examples of suitable organic surfactants having an HLB value of from 2 to 12 may be found by reference to standard publications such as McCutcheon's Detergents and Emulsifiers, MC Publishing (2002).

The water phase of the composition of the present invention may be simply water, or may contain water-soluble cosmetically acceptable components provided that the emulsion is not destabilized or inverted therein. Examples include humectants, including propylene glycol, butylene glycol, pentylene glycol, glycerin, sodium pyrrolidone carboxylic acids, citric acid, lactic acid and derivatives thereof; vitamins; preservatives, such as methyl paraben; electrolytes, such as NaCl and magnesium sulfate; and sunscreens, such as phenylbenzimidazole sulfonic acid. The water phase comprises up to about 80 weight percent, and preferably up to about 60 weight percent of the composition, and at least about 5 weight percent of the composition.

The composition can also contain effective amounts of optional cosmetically acceptable thickeners or other components such as cellulose derivatives, organically modified clays, and organic thickeners to achieve desired properties such as viscosity, stability or after-feel. Specific examples of such components are well known to cosmetic chemists. Some examples of water phase components include: magnesium aluminum silicate, hydroxyethyl cellulose, xanthan gum, and cationic cellulosic resins. Non-limiting examples of oil phase thickeners include: quatemium-18 hectorite, glyceryl trihydroxy stearate, aluminum stearate, dextrin palmitate, dimethicone crosspolymers, and polysilicone resins.

To make the emulsified cosmetic compositions of the present invention, one simply (1) stirs thoroughly together all the components of the oil phase and the surfactant(s), (2) disperses the hydrophobic alkylphosphonic acid treated pigments in the oil phase utilizing a high speed disperser or high shear mill and then (3) stirs in the water phase including any components dissolved in the water phase. Any standard high-speed stirring or homogenizing apparatus known to the art can be used to carry out the emulsification operation.

In another preferred embodiment, lipophilic alkylphosphonic acid treated pigments and fillers, or more preferably, simultaneously hydrophobic and lipophilic alkylphosphonic acid treated pigments and fillers are dispersed in an anhydrous powder-cream composition. As known to cosmetic chemists, anhydrous powder-cream products are typically formulated with a combination of ingredients including: pigments (at levels >35%); light, dry-feeling oils having good pigment wetting properties; non-tacky waxes; and optional spherical filler particles to aid in slip characteristics. The resulting foundation, blush, or eyeshadow composition is prepared by first mixing the ingredients at temperatures that are sufficiently high so as to melt the waxes, and then by pouring the molten formula as a fluid to form a creamy mass, cake, or stick. The resultant product is applied to the skin like a cream, but it is characterized as having the non-greasy feel of a powder.

U.S. Pat. No. 4,578,266 describes powder-cream compositions where hydrophobic polysiloxane treated pigments are utilized in a product containing at least 10% of dimethylpolysiloxane (optionally in combination with organically modified or cyclic polysiloxanes) to improve the dispersability of said pigment. Although polysiloxane coatings improve pigment wetting and dispersion in the claimed dimethylpolysiloxane containing composition, they do not optimize wetting in many of the other vehicles that are commonly utilized in anhydrous cosmetic cakes, creams, and sticks (such as hydrocarbons, fatty alcohols, fatty esters, sterols and sterol esters). U.S. Pat. Nos. 4,877,604 and 5,108,736 similarly describe the use of titanate-coatings to aid in the dispersion of inorganic pigments, but loadings in excess of 35% by weight (as is desirable for anhydrous powder-cream products) are not achieved.

The current invention overcomes the deficiencies of the prior art through the use of silicon-free and titanate-free alkylphosphonic acid coated pigments, where the treated pigments are preferably lipophilic; and even more preferably, where the treated pigments are simultaneously lipophilic and hydrophobic. In either case, the alkyl phosphonic acid treated pigments and fillers are dispersed in a combination of cosmetically acceptable waxes and oils at a level of 35% to 75% by weight of the formula, and preferably from 50% to 60% by weight to form a powder-cream product; that is, a product which is applied to the skin as a cream but has the non-greasy feel of a powder. Surprisingly, certain metal oxide pigments (red iron oxide is a specific example) that are treated with an alkylphosphonic acid are observed to wet more easily than those treated with an analogous alkylsilane compound.

Non-limiting examples of suitable oils for use in the powder-cream compositions of the present invention include: liquid esters of $C_{3-22}$ fatty alcohols and acids, such as isopropyl palmitate, isopropyl isostearate, ethylhexyl palmitate, isostearyl neopentanoate, octyldodecyl isostearate, etc.; liquid glyceryl esters of $C_{3-22}$ fatty acids, such as glyceryl triethylhexanoate or glyceryl triisostearate; liquid propylene glycol esters, such as propylene glycol dicaprylate/dicaprate; liquid neopentyl glycol esters, such as neopentyl glycol dicaprylate/dicaprate; liquid pentaerythritol esters, such as pentaerythrityl dicaprate/dicaprylate; liquid fatty alcohols; organically modified siloxanes, such as cetyl dimethicone, phenyl trimethicone, or caprylyl trimethicone; dimethylpolysiloxanes, cyclic polysiloxanes, such as cyclopentasiloxane, cyclotetrasiloxane; and hydrocarbons, such as mineral oil, squalane, synthetics (e.g. hydrogenated polydecene, hydrogenated polyisobutene), mixed isoparaffins, isodecane, isododecane, and isohexadecane.

Waxes are used in the claimed powder-cream compositions at a level of 5-25% and preferably 10-16% to provide structure, form, and stability to the product. Suitable waxes include those known to cosmetic chemists such as carnauba wax, candelilla wax, japan wax, beeswax, rice bran wax, montan wax, paraffin, ceresin, ozokerite, microcrystalline wax, polyethylene, polyethylene/polyvinyl acetate copolymer, polyethylene/polyacrylic acid copolymer, $C_{16-36}$ glyceryl esters, >$C_{22}$ fatty alcohols, lanolin and lanolin waxes. Organically modified silicone waxes such as $C_{20-24}$ Alkyl Methicone, $C_{24-28}$ Alkyl Methicone, $C_{30-45}$ Alkyl Methicone, Stearyl Dimethicone, Biphenyl Dimethicone, Stearoxy Dimethicone, $C_{20-24}$ Alkyl Dimethicone, or $C_{24-28}$ Alkyl Dimethicone may also be used.

The composition may also contain oil soluble wetting agents to further enhance the compatibility of the pigments and fillers with the oily vehicle. Cosmetically suitable wetting agents include: sorbitan esters, such as sorbitan sesquioleate, sorbitan trioleate, sorbitan triisostearate; polyglyceryl esters, such as polygylceryl-3 diisostearate, polyglyceryl-10 decaisosterate, polyglyceryl-10 decaoleate, polyglyceryl-3 ricinoleate, etc.; and polyhydroxystearic acid and its esters.

Fillers used in powder-cream compositions to enhance texture and provide the sensation of a dry feel are optionally treated with alkylphosphonic acid and include: talc, mica, sericite, kaolin, calcium carbonate, magnesium carbonate, silica, magnesium silicate, calcium silicate, spherical nylon, spherical polymethylmethacrylate, spherical polyurethane, or equivalent materials.

Other anhydrous products, well known to cosmetic chemists, include-lipsticks, lip glosses, and lip liners. Lipsticks are based on a wax/oil matrix formulated to be poured into molds to form a stick that is inserted into a swivel-up case. The lipstick product must have sufficient rigidity to resist breakage during use, yet it must provide easy payoff permitting deposit of the product on the lips. Pigment is generally added as a dispersion in one of the formula oils, pre-ground by techniques known to those skilled in the art, such as milling using a three roll mill or ball mill. Lip glosses are similar but softer formulas, containing less wax, packaged in pots or vials. Lip liners are harder products, containing higher percentages of waxy materials than lipsticks, packaged as pencils, formed by extrusion or hot pour techniques or as sticks filled hot into molds by gravity or injection molding. Traditional lipsticks generally contain higher viscosity, better wetting oils, combined with far lower (approximately 0-30%) pigment levels than do the powdercream products. Consequently, optimization of pigment wetting, although relevant, is less critical an issue in the composition of lipsticks than in the composition of powdercream products. Difficulty in obtaining uniform wetting and color development of the range of pigments utilized in lip products is, however, encountered, due to the differences in physical properties among the various pigments utilized to achieve all the shades required by fashion. Pigments permitted for general cosmetic use in the Code of Federal Regulations Title 21 Parts 73 and 74 are utilized. Part 73 contains the colorants not subject to certification by FDA, the naturals and inorganic pigments. Generally the inorganic pigments are more hydrophilic and less lipophilic due to their oxide nature. In contrast, the synthetic organic pigments listed in 21 CFR Part 74 (colorants subject to certification) are more lipophilic and less hydrophilic due to their organic nature. Consequently, the organic pigments wet more easily in the oil based lipstick compositions than do the inorganic pigments, resulting in easier, more complete color development. The task of the cosmetic chemist is to achieve uniform wetting of all colorants, so that the mass tone of the cosmetic seen by the customer at point of purchase is equivalent to the write off observed during use.

In another preferred embodiment of the present invention, the treated inorganic pigments for lipstick products are lipophilic, and in another particularly preferred embodiment, the treated pigments are simultaneously lipophilic and hydrophobic. In either case, the alkyl phosphonic acid treated inorganic pigments and fillers are dispersed alone or in combination with certified organic colorants in a combination of cosmetically acceptable waxes and oils at a level of 0-35% by weight of the formula, and preferable from 1-20% by weight to form a lip product whose mass tone is equivalent to the color seen following application to the lips.

Examples of suitable oils comprising about 20% to about 90% of the lip product compositions include, but are not limited to: hydrocarbons, such as mineral oil, squalane, hydrogenated polydecene, polydecene, triglycerides, such as caprylic/capric triglyceride, tricaprylin, triisostearin, natural oils, such as castor oil, rapeseed oil, sesame oil, coconut oil, safflower oil, avocado oil, soybean oil, fatty alcohols, such as oleyl alcohol, isostearyl alcohol, isocetyl alcohol, octyldodecyl alcohol, stearyl alcohol, cetyl alcohol, lanolin alcohol, fatty acids, such as isostearic acid, stearic acid, palmitic acid, myristic acid, and fatty acid esters, such as isopropyl myristate, isopropyl palmitate, isopropyl isostearate, isopropyl lanolate, ethylhexyl palmitate, cetearyl ethylhexanoate, hexadecyl stearate, tridecyl trimellitate, diisopropyl dimer dilinoleate, diisostearyl dimer dilinoleate, triisocetyl citrate, triisostearyl citrate, diisostearyl fumarate, triisostearyl trimer trilinoleate, octyldodecyl myristate, octyldodecyl stearate, octyldodecyl stearoyl stearate, isostearyl stearoyl stearate, isocetyl stearoyl stearate.

The composition may also contain oil soluble wetting agents to further enhance the compatibility of the pigments and fillers with the oily vehicle. Cosmetically suitable wetting agents include: sorbitan esters, such as sorbitan sesquioleate, sorbitan trioleate, sorbitan triisostearate, polyglyceryl esters, such as polygylceryl-3 diisostrearate, polyglyceryl-10 decaisosteatate, polyglyceryl-10 decaoleate, polyglyceryl-3 ricinoleate, etc., and polyhydroxystearic acid and its esters.

Waxes are used in the claimed lip product compositions at a level of 3-25% and preferably 10-16% to give structure, form, and stability to the product. Suitable waxes include those known to cosmetic chemists: camauba wax, candelilla wax, beeswax, japan wax, rice bran wax, montan wax, paraffin, ceresin, ozokerite, microcrystalline wax, polyethylene, polyethylene/polyvinyl acetate copolymer, polyethylene/polyacrylic acid copolymer, $C_{16-36}$ glyceryl esters, >$C_{22}$ fatty alcohols, and lanolin and lanolin waxes. Organically modified silicone waxes such as $C_{20-24}$ Alkyl Methicone, $C_{24-28}$ Alkyl Methicone, $C_{30-45}$ Alkyl Methicone, Stearyl Dimethicone, Behenyl Dimethicone, Stearoxy Dimethicone, $C_{20-24}$ Alkyl Dimethicone, or $C_{24-28}$ Alkyl Dimethicone may also be used.

Fillers used in lip product compositions to enhance texture, provide the sensation of body, and to improve wear are optionally treated with alkyl phosphonic acid and include: talc, mica, sericite, kaolin, calcium carbonate, magnesium carbonate, silica, magnesium silicate, calcium silicate, spherical nylon, spherical polymethylmethacrylate, spherical polyurethane, or equivalent materials.

Pigments used in lip products include inorganic pigments, some or all of which are treated with n-octylphosphonic acid, such as titanium dioxide, zinc oxide, iron oxides, manganese violet, natural pigments, such as carmine, organic lake pigments, such as FD&C Blue #1 Lake, FD&C Yellow #5 Lake, FD&C Yellow #6 Lake, FD&C Red #40 Lake, D&C Red #6 Lakes, D&C Red #7 Lakes, D&C Red #21 Lake, D&C Red #27 Lake, D&C Red #33 lakes organic toners, such as D&C Red #6, D&C Red #7, D&C Red #30, D&C Red #36, and pearlescent pigments such as bismuth oxychloride, metal oxide coated micas, and other composite flake pigments, and mixtures thereof.

As known to cosmetic chemists skilled in the art, cosmetic pressed powders are another vehicle for delivery of color to the face. Pressed powders are popular forms for foundation (flesh toned face color), finishing powder to set makeup, blush, and eyeshadow.

Pressed powders are formed of cosmetically acceptable filler pigments, coloring pigments, dry binders, wet binders (generally oily in nature); and optionally, preservatives, fragrance, or active ingredients. Pressed powders are manufactured by combining the dry ingredients and subjecting the pigments to sufficient agitation to achieve adequate particle size reduction, then spraying on the wet binders while continuing agitation to insure a uniform distribution of the wet binder. The finished product is pressed into pans using suitable equipment such as powder presses supplied by Kemwall, Inc. of Brooklyn, N.Y. or Cavalla, Inc. of Hackensack, N.J. The task of the cosmetic chemist is to create a finished product that provides sufficient payoff when rubbed by finger, sponge applicator, or powder puff to deposit a sufficient amount of color on the desired part of the face, yet one that also withstands the mechanical stress of shipping and transport in women's handbags without breakage. Composition techniques known to those skilled in the art consist of balancing amounts of conventional fillers, pigments, specialty fillers, pigments, and wet and dry binders to achieve the required performance.

The most common fillers used in pressed powders are talc and mica. Examples of others include but are not limited to sericite, bismuth oxychloride, boron nitride, starches and derivatives, spherical nylons, polymethylmethacrylate, polyurethane, polyethylene, polyethylene/polyacrylate copolymer, lauroyl lysine, spherical silica, polyvinylidene copolymer.

Dry binders include metallic soaps of fatty acids, such as zinc stearate, magnesium stearate, lithium stearate, magnesium myristate, and zinc myristate, kaolin, calcium silicate, porous acrylate copolymers, calcium carbonate, magnesium carbonate, magnesium trisilicate, and powdered polyethylene.

Pigments used in pressed powders depend on the specific application and can include inorganic pigments, such as titanium dioxide, zinc oxide, iron oxides, manganese violet, chromium oxide, chromium hydroxide, ferric ferrocyanide, natural pigments, such as carmine, organic lake pigments, such as FD&C Blue #1 Lake, FD&C Yellow #5 Lake, FD&C Yellow #6 Lake, FD&C Red #40 Lake, D&C Red #6 Lakes, D&C Red #7 Lakes, D&C Red #27 Lake, D&C Red #33 lakes organic toners, such as D&C Red #6, D&C Red #7, D&C Red #30, D&C Red #36, and pearlescent pigments such as bismuth oxychloride, metal oxide coated mica pigments, and other composite flake pigments, and mixtures thereof.

In another preferred embodiment of the present invention, one or more of the fillers and/or pigments are treated with an alkyl phosphonic acid compound, rendering them hydrophobic and lipophilic. The skin feel of powders formulated with alkyl phosphonic acid treated pigments and fillers is notably smoother and more moist feeling than untreated pigments. The hydrophobic nature of alkyl phosphonic acid treated pigments and fillers can be utilized to formulate wet/dry foundations, that is, products that can be applied to the skin either with a dry or wet applicator without adversely affecting the integrity of the cake. Compression of powders containing fillers and pigments, but most particularly fillers, coated with alkyl phosphonic acid is greatly enhanced.

Wet binders that can be utilized in the subject powders include but are not limited to mineral oil, polydecene, hydrogenated polydecene, squalane, synthetic esters, such as isopropyl myristate, isopropyl palmitate, ethylhexyl palmitate, cetearyl ethylhexanoate, isopropyl isostearate, octadecyl myristate, diisopropyl dimer dilinoleate, octadecyl stearate, hexadecyl stearate, octyldodecyl stearoyl stearate, hexadecyl stearoyl stearate, isostearyl stearoyl stearate, dioctyl malate, dioctyl maleate, diisostearyl malate, di-PPG-3 myristyl ether adipate, propylene glycol dicaprylate/dicaprate, coco triglycerides, caprylic/capric triglyceride, and silicone oils, such as dimethicone, phenyl trimethicone, caprylyl trimethicone, cetyl dimethicone, fatty alcohols, such as hexadecyl alcohol, isostearyl alcohol, and octyldodecanol, and natural oils, such as jojoba oil, avocado oil, apricot kernel oil, and sesame oil.

Small amounts of waxes, such as ceresin, candelilla, lanolin alcohol, or silicone wax may be added to the wet binder to enhance compression, as may small amounts of oil soluble wetting agents, such as sorbitan oleate, sorbitan isostearate, polyglyceryl-3 diisostearate, polyglyceryl-10 decaoleate, polyglyceryl-3 ricinoleate, dimethicone copolyols, and alkyl dimethicone copolyols.

The invention will be described further in the following examples, which should be interpreted as illustrative rather than limiting. Amounts identified are by weight percent unless otherwise indicated.

EXAMPLE 1

Example 1 relates to the preparation of simultaneously hydrophobic and lipophilic n-octylphosphonic acid treated titanium dioxide powders for use in cosmetic compositions: n-octylphosphonic acid vs. comparative compounds.

Pigmentary grade titanium dioxide powder (AHP-328 from Whittaker, Clark, and Daniels, Inc.; 9 m$^2$/g surface area; CAS# 13463-67-7) was surface treated with various levels of n-octylphosphonic acid (NOPA; 98% from Alfa-Aesar; CAS# 4724-48-5), and the resultant powders were tested for hydrophobicity and lipophilicity.

The powders were dry-blended with slurries containing 16.67% NOPA by weight in distilled water, and with solutions containing 24.86% by weight NOPA in 70/30 (v/v) isopropyl alcohol/water (IPA). Comparative powders were also prepared with n-octanoic acid (Aldrich Chemical Company; CAS# 124-07-2), and with n-octyltriethoxysilane (NOS; Aldrich Chemical Company; CAS# 2943-75-1).

The NOPA/water slurry was prepared by dispersing NOPA crystals in water under ambient conditions, and by oven-annealing the slurry in a closed container at a temperature of 70° C. for a time sufficient so as to yield a pourable, translucent, partial-solution of NOPA in water. NOPA was similarly mixed with IPA to yield a completely soluble solution at room temperature. The octanoic acid and NOS compounds were used as received in their neat liquid forms.

Various levels of each liquid were separately dispensed over pre-weighed aliquots of powder (5 g). The aliquots were dry-mixed with a hand-held spatula under ambient conditions in separate glass jars. The spatula was used to agitate and press the powder against the side of the glass jar to achieve complete wetting. With the exception of the water-based slurry, the liquids were dispensed under ambient conditions. The water-based slurry was pre-heated to 70° C. as described above, and was applied while hot (over the ambient powder) to facilitate mixing. After blending, most of the powders were oven-dried in open containers for 24 hours at a temperature of 80° C. The only exceptions were the powders that were treated with water-based NOPA slurries—they were dried at 102° C. for 24 hours. The surface treated powders were removed from the oven, and were stored in closed containers under ambient conditions for later use.

The following procedure was used to determine relative hydrophobicity: 0.05 g of each powder was weighed into separate glass jars together with 10 g of distilled water. The mixtures were then vigorously shaken by hand, and the closed containers were set on a horizontal surface for visual observation. The most hydrophobic powders were observed to climb the walls of the glass jars and to float on the surface of the water. The least hydrophobic samples were observed either to coalesce and sink to the bottom of the container, or to disperse in the water phase.

The following procedure was used to determine the relative lipophilicity: approximately 2.0 g aliquots of each powder were weighed into separate glass jars together with an appropriate level of a liquid carrier to yield slurries containing 14.26% solids by weight. The liquid carriers included two oils that are commonly used in cosmetic compositions: decamethylcyclopentasiloxane (DC245 from Dow Corning Corporation, CAS# 541-02-6), and ethylhexylpalmitate (EHP from Trivent, Inc., CAS# 29806-73-3). The slurries were vigorously shaken by hand, and then were allowed to equilibrate under ambient conditions at room temperature for a period of 4 to 6 hours. After equilibration, the slurries were again vigorously shaken, and while dispersed, aliquots of the slurries were pipeted and weighed into 10 ml graduated cylinders that were pre-tarred on an analytical balance. The cylinders were filled with 10 ml aliquots, which equated to approximately 10 g of slurry in each case. The graduated cylinders were then set on a horizontal surface under ambient conditions, and the volumes of the sediments were monitored over time. The final sediment volumes were reported once no change was observed for one week (the duration of the entire settling process was typically two to three weeks).

Settling volume is a measure of the relative dispersablity of a powder in a liquid medium. Higher sediment volumes (lower sediment densities) are representative of poor dispersions, whereas lower sediment volumes (higher sediment densities) are representative of better dispersions. Generally, the better dispersions are less likely to agglomerate, and thus they are able to settle into tighter compacts with less interstitial space. Thus, the sediment volume is a relative measure of the degree to which the powder particles are deagglomerated and effectively wetted by the dispersing media. In these cases, the media were hydrophobic oils, so the more lipophilic powders produced the best dispersions (least agglomeration), and the lowest sediment volumes.

Table 1 provides the surface treatment concentrations together with qualitative rankings of hydrophobicity, and final sediment volumes (representing lipophilicity).

powder over 10 g water). After approximately one month of aging under ambient conditions, it was noted that, even in the presence of water, the hydrophobicity of the 1% NOPA and 2% NOPA treated samples remain unchanged. Thus, the NOPA treatment is surprisingly resistant to hydrolysis in spite of the fact that the powders were originally treated from a water-based NOPA slurry.

Collectively, these results show that at the appropriate level of surface treatment, NOPA is capable of providing simultaneous hydrophobic and lipophilic characteristics that are surprisingly comparable to those achieved with NOS. For example, 1% NOPA treated powder behaves similarly to 2.0% NOS treated powder in both the hydrophobic and lipophilic tests. The optimum level of NOPA for this particular powder is between 1.0% and 2.0% by weight as judged by both sedimentation and hydrophobicity results. However, both the hydrophobic and lipophilic characteristics are also improved at lower levels (as judged by the 0.5% examples). Higher levels (as judged by the 4.0% examples) lead to an unexpected loss of hydrophobicity with a simultaneous retention of lipophilic properties. This result reaffirms that there is an optimum level of NOPA beyond which the powder loses its simultaneous lipophilic and hydrophobic characteristics. Interestingly, octanoic acid provides an improvement in lipophilicity, but hydrophobicity is not greatly improved. Thus, although the alkyl chain lengths of all three comparative molecules are $C_8$ in length, and although all three are bound to the surface of the titanium dioxide particles (as can be seen by the increase in settling densities when compared to untreated

TABLE 1

Hydrophobicity and lipophilicity comparisons of titanium dioxide; surface treated with NOPA, NOS, and octanoic acid.

| Surface Treatment & Concentration (% active ingredient by weight powder) | Surface treatment Vehicle | Relative Hydrophobicity 1 = hydrophobic (repels & floats on water) 2 = partially hydrophobic 3 = coalesces and sinks 4 = disperses | Lipophilic Dispersion Medium | Final Sediment Volume (ml) |
|---|---|---|---|---|
| 0 | None | 4 | EHP | 7.4 |
| 0.5% NOPA | 70/30 IPA/water | 2 | EHP | 3.1 |
| 1.0% NOPA | 70/30 IPA/water | 1 | EHP | 3.1 |
| 2.0% NOPA | 70/30 IPA/water | 1 | EHP | 3.6 |
| 4.0% NOPA | 70/30 IPA/water | 4 | EHP | 3.4 |
| 2.0% octanoic acid | Neat | 4 | EHP | 2.6 |
| 2.0% NOS | Neat | 1 | EHP | 3.0 |
| 0 | None | 4 | DC245 | 9.4 |
| 0.5% NOPA | Water | 2 | DC245 | 3.2 |
| 1.0% NOPA | Water | 1 | DC245 | 2.7 |
| 2.0% NOPA | Water | 1 | DC245 | 2.7 |
| 4.0% NOPA | Water | 4 | DC245 | 3.8 |
| 0.5% NOPA | 70/30 IPA/water | 2 | DC245 | 3.2 |
| 1.0% NOPA | 70/30 IPA/water | 1 | DC245 | 2.6 |
| 2.0% NOPA | 70/30 IPA/water | 1 | DC245 | 2.8 |
| 4.0% NOPA | 70/30 IPA/water | 4 | DC245 | 3.2 |
| 0.5% NOS | Neat | 2 | DC245 | 4.0 |
| 1.0% NOS | Neat | 1 | DC245 | 2.9 |
| 2.0% NOS | Neat | 1 | DC245 | 2.3 |
| 4.0% NOS | Neat | 1 | DC245 | 2.2 |

The NOPA treated titanium dioxide powders were also examined after one month of aging in the presence of water. Samples having surface treatment concentrations of 0%, 0.5%, 1%, 2%, and 4% NOPA by weight were prepared from water based NOPA slurries (16.67% by weight), and were dried for 24 hours at 102° C. The hydrophobicity of each sample was evaluated as previously described (using 0.05 g powder), the hydrophobic characteristics are surprisingly different. Thus, lipophilicity and molecular structure cannot be used as predictors of hydrophobicity. Also, given that NOPA is not known to polymerize (as NOS does), it is even more surprising to observe that NOPA displays these simultaneous characteristics. Moreover, this also means that polymerizability is neither a predictor, nor is it a prerequisite for hydrophobicity. Thus, given that the best pigments for this invention are those that are simultaneously hydrophobic and lipophilic, and given that n-octylphosphonic acid treated pigments perform surprisingly well in both respects, it appears that NOPA treated pigments are surprisingly well suited for use in the cosmetics compositions of this invention.

It is equally surprising to note that the NOPA treated pigments exhibit similar hydrophobic and lipophilic characteristics, independent of the vehicle that was used during their preparation. For example, even though NOPA is only partially soluble in water, the powders treated with water-based vehicles behave the same as those treated with IPA vehicles (where the NOPA is completely soluble).

Thus, the pigments as employed in the present invention are preferably simultaneously hydrophobic and lipophilic independent of whether they have been treated from solvent based or water based media (as long as the surface coverage is within the range as defined herein); as such, pigments prepared by either method are ideal for use in the cosmetics compositions of this invention. Moreover, unlike the surface treated pigments of the prior art, the simultaneously hydrophobic/lipophilic pigments as employed in the present invention can be prepared (if so desired) from water based media whereby the resulting powders (and the cosmetics compositions that contain them) are by definition devoid of the deleterious VOC's and reaction by-products that otherwise may taint the surfaces of prior-art treated powders (as well as the cosmetics compositions that contain them).

Ignoring the potential for the evaporation of the compounds themselves, those skilled in the art can readily calculate that the theoretical weight loss following hydrolysis and complete condensation is 40.21% for neat NOS (where the volatile components would be ethanol and water), 71.79% for prehydrolyzed NOS (where the volatile components would be predominantly ethanol and water), and 83.33% for the NOPA/water slurry (where the volatile component is theoretically only water). The results of this experiment are presented in Table 2.

TABLE 2

Comparative volatilities of NOS, prehydrolyzed NOS, and NOPA after 24 hours at 80° C.

| Sample | Starting Weight | Residual weight | Theoretical Residual Weight | Residual Weight as a percentage of Theoretical | % actual weight loss |
|---|---|---|---|---|---|
| NOS (neat) | 0.3343 g | 0.0106 g | 0.1998 g | 5.3% | 96.8% |
| Prehydrolyzed NOS (47.17% active) | 0.5728 g | 0.1280 g | 0.1615 g | 79.25% | 77.6% |
| NOPA (16.67% active) | 0.6839 g | 0.1025 g | 0.1139 g | 89.99% | 85.0% |

When compared to NOS and prehydrolyzed NOS, these results demonstrate that the NOPA/water slurry retains a higher level of residual weight (89.99% of theoretical) after evaporation of its liquid carrier. Moreover, unlike the other treatments (where ethanol is evolved as a VOC), water is theoretically the only component that is volatilized from the NOPA/water slurry. In addition, the actual residual weight from neat NOS is far less than its theoretical value, which indicates that besides the evolution of ethanol as a VOC, the NOS molecule itself is volatile under these conditions. The prehydrolyzed NOS exhibits much less volatility than neat NOS, but its volatile component is still comprised of ethanol from both the condensation reaction, and from the excess ethanol that was used as a carrier. Thus, when compared to other surface treatments, NOPA has the advantages of being relatively non-volatile, of being applicable in a VOC-free water-based medium, and of being free of VOC reaction by-products. The absence of VOC's (particularly alcohols and especially primary alcohols) is advantageous for the preparation of contaminant-free pigments, which are desirable components for use in the cosmetics compositions of the present invention.

EXAMPLE 2

Example 2 relates to volatility comparisons between NOPA, NOS, and pre-hydrolyzed NOS. An experiment was performed for the purpose of determining the relative volatility of NOPA, neat NOS, and a pre-hydrolyzed version of NOS. The NOPA was prepared as a 16.67% by weight slurry in water as described in Example 1. The pre-hydrolyzed version of NOS was prepared according to procedures outlined in U.S. Pat. No. 5,348,760; where NOS was mixed with ethanol, water, and acetic acid at a weight ratio of 50/50/5/1 to yield the hydrolyzed oligomeric species (47.17% active). Quantities of each liquid were weighed into pre-weighed aluminum pans, using an analytical balance with accuracy to four decimal places. The pans were then placed into a forced air oven at 80° C. for a period of approximately 24 hours to simulate drying conditions that could be used during a surface treatment production process (this temperature also falls within the range of temperatures that could be used in preparing the oil phase of the present invention—with the surface treated particulates dispersed therein).

EXAMPLE 3

Example 3 relates to the durability of NOPA treated inorganic pigments. The titanium dioxide of Example 1 was treated with 2% by weight NOPA from a 16.67% NOPA/water slurry via procedures outlined in Example 1. Following the procedures of Example 1, the resulting hydrophobic powder was dispersed in EHP (a common oil that is used in cosmetics compositions), and the dispersion was weighed into a 10 ml graduated cylinder for the purpose of conducting a sedimentation experiment. The graduated cylinder was sealed with a glass stopper, and the dispersion was initially allowed to settle to its final sediment volume under ambient conditions. The clear supernatant was then pipeted from the cylinder, and fresh EHP was added. The cylinder was resealed, and vigorously shaken by hand for the purpose of redispersing the sediment. This "first wash" sediment was then allowed to resettle to its final sediment volume. The process was then repeated in a "second wash" (the supernatant was removed, fresh EHP was added, and the sediment was re-dispersed), but this time the sealed graduated cylinder was placed in an oven at 80° C., where the slurry was allowed to settle for a period of 24 hours.

This temperature was chosen because it falls within the range of temperatures that could be employed during the process of mixing the ingredients that comprise the oil phase of an oil-in-water emulsion, a water-in-oil emulsion, or an anhydrous cosmetic composition, where one or more of the ingredients could include surface treated particulates of the type defined by this invention. Consequently, it is important for the surface treatment to remain intact and adsorbed on the particle surfaces, otherwise the dispersion stability of the final cosmetic composition may be compromised. Thus, in order to test the durability of the NOPA treated pigment, the washing and settling processes were repeated at 80° C. for two additional cycles, and then once more under ambient conditions.

Using the ratio of NOPA-treated powder to liquid in this experiment, the effective level of NOPA equates to 0.33% by weight EHP. In a separate test, neat NOPA was determined to be soluble in EHP at the 0.33% level (both at 80° C. and under ambient conditions). Similar experiments on other inorganic powders have shown solvent washing will not remove a strongly adsorbed surface treatment, even when the surface treatment itself is highly soluble in the dispersion medium (Parker et al. in *Material Research Society Symposium Proceedings*, 249, 1992, pp.273-278). On the other hand, when the adsorbed molecules are weakly bound, solvent washing will readily remove the surface treatment from the powder, and the resultant sediment volume will increase with each successive solvent wash.

In this experiment, the durability of the NOPA treatment was tested by solvent washing NOPA treated powder with an otherwise good solvent for NOPA under both ambient conditions, and at 80° C. The results are presented in Table 3.

TABLE 3

The effect of solvent washing on the sediment volume of NOPA treated titanium dioxide dispersed in EHP.

| Solvent Wash Cycle | Temperature During Sedimentation Experiment | Final Sediment Volume (ml) |
|---|---|---|
| 0 (initial) | Ambient | 3.5 |
| 1 | Ambient | 3.2 |
| 2 | 80° C. | 2.6 |
| 3 | 80° C. | 2.6 |
| 4 | 80° C. | 2.6 |
| 5 | Ambient | 2.6 |

These results show that the sediment volume actually decreases with successive washing cycles (up to cycle 2), beyond which there is no change in sediment volume. Thus, the NOPA is strongly adsorbed on the inorganic pigment, and it cannot be readily solvated, even when the treated powder is extracted with an otherwise good solvent for the neat compound. This shows that NOPA treated pigments can be surprisingly durable, and as such they can withstand the conditions that are likely to be encountered during the preparation of, and during the storage of a cosmetic composition. Thus the cosmetic compositions of the present invention (with alkylphosphonic acid treated particulates incorporated therein) are anticipated to be both process and storage stable.

EXAMPLE 4

Example 4 relates to alkylphosphonic acid surface treated pigments with simultaneous hydrophobic and lipophilic characteristics for incorporation into cosmetic compositions. Additional inorganic pigments were treated with NOPA, and several were tested for hydrophobicity and lipophilicity via the methods and procedures as outlined in Example 1. The pigments for this example include black iron oxide ($Fe_3O_4$, c33-134 from Sun Chemical), and red iron oxide ($Fe_2O_3$, A-1206 from Color Techniques, Inc., CAS# 1332-37-2). The pigments were treated with 2% by weight NOPA from a 16.67% by weight slurry of NOPA in distilled water via procedures similar to those described in Example 1. The NOPA slurry for this example was pre-heated to 80° C., and the treated powders were oven dried at 80° C. for 24 hours. Untreated powders were also tested for relative comparisons. The results of lipophilicity (sedimentation) and hydrophobicity experiments are presented in Table 4.

TABLE 4

Hydrophobicity and lipophilicity comparisons of 2% NOPA surface treated black iron oxide, red iron oxide and untreated powders.

| Powder | Treatment | Relative Hydrophobicity 1 = hydrophobic (repels & floats on water) 2 = partially hydrophobic 3 = coalesces and sinks 4 = disperses | Lipophilic Dispersion Medium | Final Sediment Volume (ml) |
|---|---|---|---|---|
| Red iron oxide | none | 4 | EHP | 3.8 |
| Red iron oxide | 2% NOPA | 1 | EHP | 2.4 |
| Red iron oxide | None | 4 | DC245 | 5.4 |
| Red iron oxide | 2% NOPA | 1 | DC245 | 2.1 |
| Black iron oxide | None | 4 | EHP | 7.6 |
| Black iron oxide | 2% NOPA | 1 | EHP | 2.2 |
| Black iron oxide | None | 4 | DC245 | 8.4 |
| Black iron oxide | 2% NOPA | 1 | DC245 | 2.1 |

These results show that NOPA surface treated pigments can be surprisingly hydrophobic and lipophilic—even when they have been treated from water-based media. Moreover, the hydrophobic and lipophilic characteristics occur simultaneously. Hence, NOPA treated pigments such as these (with simultaneous characteristics of hydrophobicity and lipophilicity) are useful for incorporation into the cosmetic compositions of the present invention.

EXAMPLE 5

This example relates to cosmetic compositions containing organophosphonic acid coated particulates, and describes the preparation of a water-in-oil foundation that contains simultaneously hydrophobic and lipophilic alkylphosphonic acid surface treated pigment particles. The pigments for this example were surface treated with 2% NOPA from a water-based vehicle as described in Example 1. Note that the pigments could be equivalently prepared from a solvent-based vehicle (such as IPA) if so desired.

| Ingredient | % |
|---|---|
| Phase A | |
| Cetyl PEG/PPG-10-1 Dimethicone (Abil EM-90, Degussa) | 0.45 |
| Polyglyceryl-4 Laurate, Cetyl PEG/PPG-10-1 Dimethicone, Hexyl Laurate (Abil WE-09, Degussa) | 1.75 |
| Cetyl Dimethicone (Abil Wax 9814) | 1.80 |
| Propylparaben | 0.10 |
| Phase B | |
| Ethylhexyl Palmitate | 7.00 |
| Phenyl Trimethicone (DC 556 Fluid, Dow Corning) | 2.20 |
| 2% n-octyl phosphonic acid treated titanium dioxide | 7.50 |
| 2% n-octyl phosphonic acid treated yellow iron oxide | 0.70 |
| 2% n-octyl phosphonic acid treated red iron oxide | 0.35 |
| 2% n-octyl phosphonic acid treated black iron oxide | 0.03 |
| 2% n-octyl phosphonic acid treated talc | 3.82 |
| Dimethicone/viscosity 10 centistokes | 1.30 |
| Phase C | |
| Cyclomethicone, Polysilicone-11 (Gransil GCM, Grant Industries) | 15.00 |
| Phase D | |
| Deionized water | 51.85 |
| Diazolidinyl Urea (Germall II, ISP) | 0.20 |
| Sodium Chloride | 0.50 |
| Butylene Glycol | 5.30 |
| Methylparaben | 0.15 |
| | 100.00 |

The above composition was prepared as follows: The components of Phase A (the emulsifier phase) were combined with stirring. The components of Phase B (the pigment grind) were combined with high shear mixing until all of the pigment particles were dispersed, and then Phase B was added to Phase A with stirring. Phase C (the viscosity stabilizer) was added to the combined Phases A and B with stirring. The methylparaben of Phase D was pre-dissolved in butylene glycol, and then it was added along with the other Phase D ingredients to the deionized water (while stirring until all components were dissolved). Phase D (the water phase) was then slowly added to the combined Phases A, B, and C (the oil phase) while homogenizing. Homogenization was continued for 15 minutes to form the finished product, which was then filled into suitable storage containers.

It can be appreciated that this example is only illustrative, and that modified procedures and compositions as described within this invention could conceivably be used to form a variety of similar products with a broad range of end-use characteristics for use in a broad range of cosmetic applications.

EXAMPLE 6

This example describes the preparation of a powder-cream foundation containing pigments that are lipophilic, or simultaneously lipophilic and hydrophobic. The composition ingredients for this example are given as follows:

| | |
|---|---|
| Ethylhexyl palmitate | 35.05 |
| Tribehenin | 5.50 |
| $C_{30-45}$ Alkyl Methicone | 5.50 |
| $C_{20-40}$ Alcohols | 1.10 |
| Polyglyceryl-3 Diisostearate | 0.50 |
| Methylparaben | 0.20 |
| Propylparaben | 0.10 |
| BHT | 0.05 |
| 2% n-octyl phosphonic acid treated titanium dioxide | 15.00 |
| 2% n-octyl phosphonic acid treated yellow iron oxide | 1.40 |
| 2% n-octyl phosphonic acid treated red iron oxide | 0.65 |
| 2% n-octyl phosphonic acid treated black iron oxide | 0.06 |
| 2% n-octyl phosphonic acid treated talc | 14.89 |
| 2% n-octyl phosphonic acid treated sericite | 15.00 |
| Spherical nylon | 5.00 |
| | 100.00 |

The pigments were dispersed in a portion of the oil (a portion which was sufficient for wetting-out the pigment), and the dispersion was milled using a three-roll mill (a high-speed disperser, or a media mill could also have been used). The waxes and preservatives were separately dissolved in the remaining oil and heated to 95° C. until clear, and the solution was cooled to 75-80° C. The pigment dispersion was then added to the solution together with fillers, talc, sericite, and nylon; and the combination was mixed with a high-speed agitator until no agglomerates remained. The product was then stirred under vacuum to facilitate de-airing, and the resultant mixture was subsequently filled into suitable compacts at 70-72° C.

EXAMPLE 7

Example 7 relates to powdercream foundation containing lipophilic pigments, and describes the preparation of a powder-cream foundation containing pigments that are lipophilic. The composition was prepared according to the procedures of example 6. The composition ingredients for this example are given as follows:

| | |
|---|---|
| Caprylyl Trimethicone | 24.25 |
| Dimethicone/10 cs | 11.00 |
| Tribehenin | 6.00 |
| $C_{24-28}$ Alkyl Dimethicone | 6.00 |
| Polyglyceryl-3 Diisostearate | 0.75 |
| Methylparaben | 0.20 |
| Propylparaben | 0.10 |
| 2% n-octylphosphonic acid treated titanium dioxide | 15.00 |
| 2% n-octylphosphonic acid treated yellow iron oxide | 2.80 |
| 2% n-octylphosphonic acid treated red iron oxide | 1.20 |
| 2% n-octylphosphonic acid treated black iron oxide | 0.20 |
| 2% n-octylphosphonic acid treated talc | 12.50 |
| 2% n-octylphosphonic acid sericite | 15.00 |
| Aluminum Starch Octenyl Succinate | 5.00 |
| | 100.00 |

EXAMPLE 8 (COMPARATIVE)

Comparative example 8 relates to powdercream foundation containing lipophilic pigments. This example describes the preparation of a powder-cream foundation containing pigments that are lipophilic. The composition was prepared according to the procedures of example 6. The composition ingredients for this example are given as follows:

| | |
|---|---|
| Caprylyl Trimethicone | 24.25 |
| Dimethicone/10 cs | 11.00 |
| Tribehenin | 6.00 |
| $C_{24-28}$ Alkyl Dimethicone | 6.00 |
| Polyglyceryl-3 Diisostearate | 0.75 |
| Methylparaben | 0.20 |
| Propylparaben | 0.10 |
| 2% n-octylsilane treated titanium dioxide | 15.00 |
| 2% n-octylsilane treated yellow iron oxide | 2.80 |
| 2% n-octylsilane treated red iron oxide | 1.20 |
| 2% n-octylsilane treated black iron oxide | 0.20 |
| 2% n-octylsilane treated talc | 12.50 |
| 2% n-octylsilane treated sericite | 15.00 |
| Aluminum Starch Octenyl Succinate | 5.00 |
| | 100.00 |

The pretreatment in comparative example 8 was observed to render the pigments and fillers hydrophobic and lipophilic, and to enhance their wetting and dispersion characteristics when compared to untreated pigments (as did the claimed n-octylphosphonic acid pre-treatment illustrated in example 7). Surprisingly however, the pigments in example 7 were observed to wet more easily than those of example 8. Of equal importance, all of the n-octylphosphonic acid pigments unexpectedly exhibited color development prior to the high-shear agitation phase, as evidenced by the mass tone of the bulk mixture. Consequently, the time required for the milling step in example 7 was surprisingly reduced by a factor of 33% when compared to the time required for milling in example 8.

EXAMPLE 9.

Example 9 relates to lipstick containing lipophilic inorganic pigments and having the following ingredients.

| | |
|---|---|
| Castor Oil | 30.90 |
| Candelilla | 7.00 |
| Carnauba | 1.50 |
| Ceresin | 2.50 |
| Microcrystalline Wax | 3.50 |
| Octyldodecyl Stearate | 15.00 |
| Triisostearyl Citrate | 20.00 |
| Methylparaben | 0.20 |
| Propylparaben | 0.10 |
| Ascorbyl Palmitate | 0.05 |
| Pigment Grind | |
| Castor Oil | 5.00 |
| D&C Red #7 Lake | 0.03 |
| D&C Red #6 Lake | 0.17 |
| 2% n-octylphosphonic acid treated red iron oxide | 2.00 |
| 2% n-octylphosphonic acid treated titanium dioxide | 2.00 |
| 2% n-octylphosphonic acid treated black iron oxide | 0.05 |
| Pearl Pigment | |
| 2% n-octylphosphonic acid treated mica (and) titanium dioxide | 10.00 |
| | 100.00 |

The pigment grind was prepared by dispersing the pigments in castor oil and milling to a particle size of <10 microns. The waxes, oils and preservatives were combined and heated to 85-90° C. with propeller agitation until clear. The temperature was lowered to 80° C., and the pigment grind and pearl pigment were added and stirred until dispersed. The ascorbyl palmitate was added, and the bulk was filled into suitable molds at 70-72° C. The resulting sticks exhibited the same color as does the lipstick when applied to the lips.

EXAMPLE 10

This example describes pressed powder eyeshadow having the following ingredients.

| | |
|---|---|
| 2% n-octylphosphonic acid treated talc | 30.20 |
| Iron Oxides | 6.50 |
| Zinc Stearate | 5.00 |
| Methylparaben | 0.20 |
| Propylparaben | 0.10 |
| 2% n-octylphosphonic acid treated iron oxide coated mica pearlescent pigment (Colorona ® Copper) | 50.00 |
| Isopropyl Isostearate | 8.00 |
| | 100.00 |

The treated talc, pigments, zinc stearate, and preservatives were combined in a ribbon blender and pulverized with a hammer mill through a 0.027" screen. The pearlescent pigment was added to the pulverized phase in the ribbon blender, and the oil was sprayed on with agitation. The batch was passed through the hammer mill through a jump gap then pressed into suitable pans.

The resulting eyeshadow applied smoothly to the lids and exhibited good adhesion. Cake strength was surprisingly good, in spite of the high level of pearl.

EXAMPLE 11

Example 11 describes wet/dry pressed powder foundation with hydrophobic/lipophilic pigments. The foundation is made with the following ingredients.

| | |
|---|---|
| 2% n-octylphosphonic acid treated talc | 61.10 |
| 2% n-octylphosphonic acid treated sericite | 20.00 |
| 2% n-octylphosphonic acid treated titanium dioxide | 8.00 |
| 2% n-octylphosphonic acid treated yellow iron oxide | 2.00 |
| 2% n-octylphosphonic acid treated red iron oxide | 1.25 |
| 2% n-octylphosphonic acid treated black iron oxide | 0.35 |
| Zinc stearate | 3.00 |
| Methylparaben | 0.20 |
| Propylparaben | 0.10 |
| Squalane | 3.00 |
| | 100.00 |

The treated pigments and fillers were combined with the zinc stearate and preservatives in a twin shell blender equipped with an intensifier bar and mixed with intensifier bar agitation until homogenous. The squalane was added through the intensifier bar while agitating to insure even distribution. The batch was pulverized using a hammer mill (with a 0.027" screen), and was pressed into suitable pans.

The resulting pressed powder applied smoothly with good adhesion to the skin. Repeated use either with a wet or dry sponge was possible without deterioration of application properties.

The present invention has been described with particular reference to the preferred embodiments therein. It is to be appreciated that variations and modifications can be made without departing from the spirit and scope of the present invention as defined by the following claims. All U.S. patents referred to herein are incorporated by reference in their entireties.

We claim:

1. A method of preparing a cosmetic composition comprising a plurality of particulates, the method comprising:
   a) at least partially surface treating at least some of the plurality of particulates with one or more organophosphonic acids such that the organophosphonic acid on said particulates is present at a level of 2-20 µmoles/m² and the surface treated particulates are simultaneously lipophilic and hydrophobic; and
   b) mixing, blending, or dispersing the particulates together with any remaining ingredients of the cosmetic composition.

2. The method of claim 1 wherein said organophosphonic acid surface treated particulates from a) are dispersed during b) into the oil phase of a water-in-oil or oil-in-water cosmetic composition, and where said oil phase dispersion is then mixed, blended, or dispersed together with the remaining ingredients of the cosmetic composition.

3. The method of claim 1 wherein said organophosphonic acid surface treated particulates are surface treated in a) through the use of either a water based vehicle, an alcohol based vehicle, an alcohol/water blend, or a neat organophosphonic acid.

4. A method of preparing a cosmetic composition comprising surface treated particulates where at least some of said particulates are at least partially surface treated with one or more organophosphonic acids, the method comprising an integral blend method and comprising a) mixing, blending, or dispersing the particulates together with at least a portion of any remaining ingredients of the cosmetic composition to form a mixture, blend, or dispersion, and b) integrally blending an organophosphonic acid with at least a portion of the mixture, blend, or dispersion.

5. A method or preparing a cosmetic composition utilizing a plurality of particulates that have been at least partially surface treated with an organophosphonic acid.

6. The method of claim 5 wherein the organophosphonic acid is of the general formula $$R_x[PO(OH)_2]_y$$

where R is an organic group containing 1 to 50 carbon atoms, x is the number of organic groups and is in the range of 1-30, and y is the number of phosphonic acid groups and is in the range of 1-20.

7. A sunscreen composition comprising an amount of one or more sunscreens and a plurality of particulates surface treated with an organophosphonic acid.

8. The sunscreen composition of claim 7, wherein the one or more sunscreens are selected from the group consisting of octyldimethyl-PABA, octylmethoxycinnamate, benzophenones, octyl salicylate, homomenthyl salicylate, and phenylbenzimidazole sulfonic acid.

9. The sunscreen composition of claim 7, being a water-in-oil or oil-in-water emulsion.

10. The sunscreen composition of claim 9 having an oil phase comprised of one or more sunscreens selected from the group consisting of octyldimethyl-PABA, octylmethoxycinnamate, benzophenones, octyl salicylate, and homomenthyl salicylate.

11. The sunscreen composition of claim 9 having a water phase comprised of phenylbenzimidazole sulfonic acid.

12. A cosmetic composition comprising a water-in-oil emulsion having an oil phase, with a plurality of particulates surface treated with an organophosphonic acid dispersed within the oil phase.

13. A cosmetic composition comprising a plurality of particulates surface treated with an organophosphonic acid, the particulates being dispersed in a mixture of one or more cosmetically acceptable waxes and one or more cosmetically acceptable oils, the particulates being present at a level of 35% to 75% by weight of the cosmetic composition.

* * * * *